United States Patent
Ernst et al.

(10) Patent No.: US 10,688,407 B1
(45) Date of Patent: Jun. 23, 2020

(54) FRACTIONATION COLUMN WITH HEAT PUMP USING HIGH BOILING POINT VAPOR

(71) Applicant: UOP LLC, Des Plaines, IL (US)

(72) Inventors: Gregory A. Ernst, Oak Park, IL (US); Jason L. Noe, Mount Prospect, IL (US); Jason T. Corradi, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/353,579

(22) Filed: Mar. 14, 2019

(51) Int. Cl.
| | |
|---|---|
| *B01D 1/18* | (2006.01) |
| *B01D 3/00* | (2006.01) |
| *B01D 1/28* | (2006.01) |
| *C07C 7/04* | (2006.01) |
| *B01D 3/32* | (2006.01) |

(52) U.S. Cl.
CPC ......... *B01D 1/2856* (2013.01); *B01D 1/2806* (2013.01); *B01D 3/007* (2013.01); *B01D 3/322* (2013.01); *C07C 7/04* (2013.01)

(58) Field of Classification Search
CPC .... B01D 1/2856; B01D 1/2806; B01D 3/007; B01D 3/322; C07C 7/04
See application file for complete search history.

(56) References Cited

U.S. PATENT DOCUMENTS

| | | | |
|---|---|---|---|
| 3,414,484 A | 12/1968 | Carson et al. | |
| 4,230,535 A | 10/1980 | Howard | |
| 4,559,108 A | 12/1985 | Ahlberg | |
| 4,945,175 A * | 7/1990 | Hobbs | C07C 2/76 585/415 |
| 7,981,256 B2 * | 7/2011 | Wegerer | B01D 3/14 202/153 |
| 9,045,697 B2 * | 6/2015 | Sadler | C07C 7/04 |
| 2007/0017291 A1 * | 1/2007 | Cypes | B01D 3/00 73/590 |

* cited by examiner

*Primary Examiner* — Youngsul Jeong
*Assistant Examiner* — Gabriel E Gitman

(57) ABSTRACT

Process and apparatus ensure high on-stream reliability of a complex that requires a heat pump which is using a compound having a high boiling point, such as xylenes. When the compressor is shutdown, it can be isolated from the distillation column and receiver while the column is allowed to continue to operate with an auxiliary reboiler for constant heat input. The heat pump can be started up and heated to the normal process temperature, so that when the heavy vapor is charged to the heat pump, it does not immediately condense into liquid, causing damage to the compressor.

17 Claims, 1 Drawing Sheet

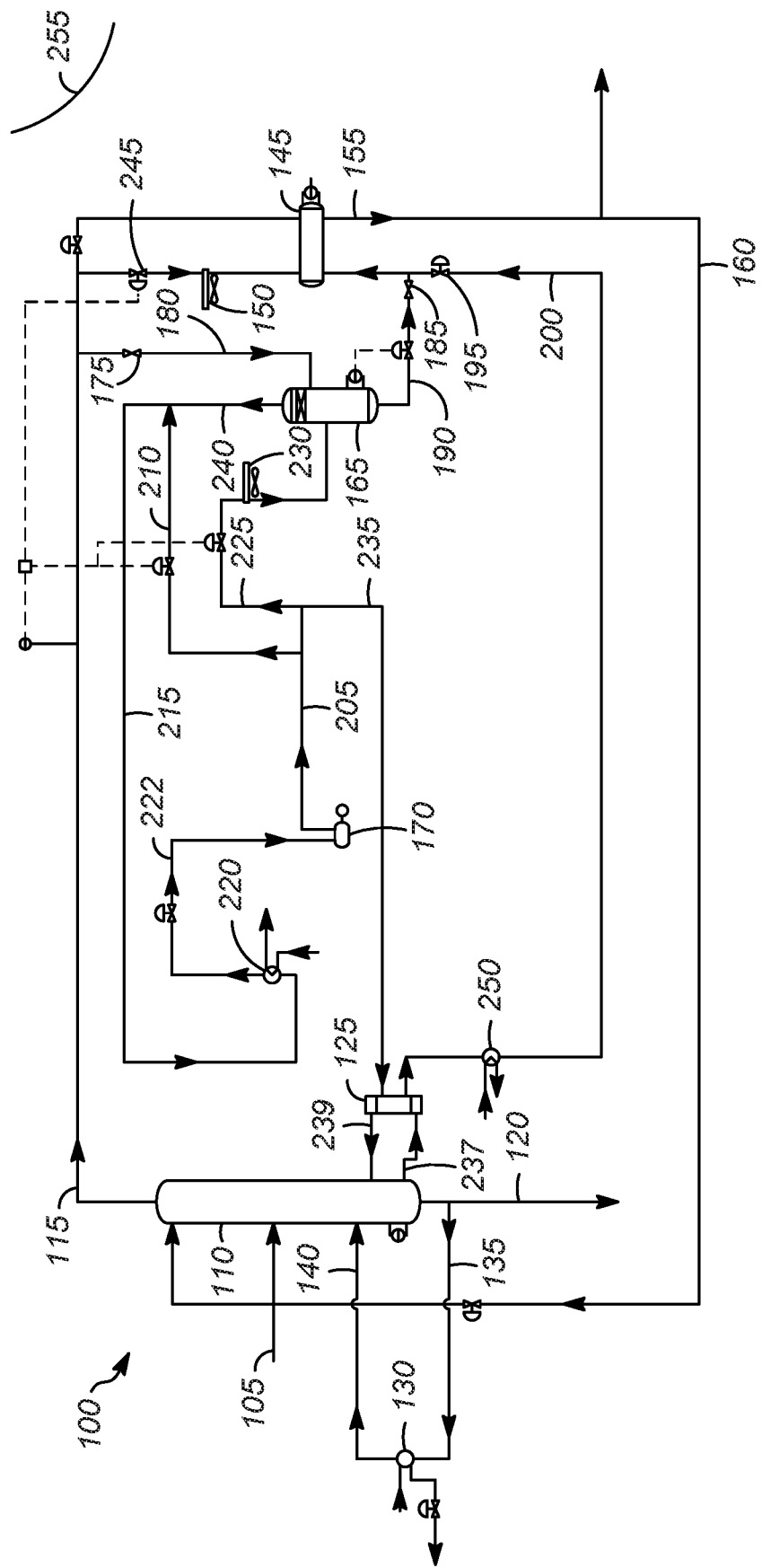

FRACTIONATION COLUMN WITH HEAT PUMP USING HIGH BOILING POINT VAPOR

Heat pump systems are used to provide both a condensing and reboiling function in commercial operating distillation columns. The applications where they are used are typically for components with low boiling points and low molecular weights. These compounds tend to be a vapor at temperatures at or below 0° C., and have a boiling point at or below 0° C. Examples include, but are not limited to, separating propane from propylene or normal butane from isobutane. In these systems, the condensing medium is typically admitted to the column as a vapor, so there is little concern about condensation in the heat pump compressor. Furthermore, it is straightforward to ensure that the suction section of the heat pump is free of liquid prior to starting the heat pump compressor. Sending liquid to a compressor, or allowing condensation to occur in the compressor may damage the compressor, requiring shutdown and possibly replacement. In systems using a low molecular weight component or a low boiling point component, a single drum can be used both as a receiver and for knockout function, enabling removal of entrained liquid droplets from a flowing vapor stream, because startup of the column does not require the removal of liquid or special precautions to ensure liquid does not form through a cold compressor.

However, in applications using compounds having a higher boiling point and/or higher molecular weight, it becomes more difficult to ensure that all liquid has been removed from the suction side of a compressor, and to ensure that the compressor and associated piping has been warmed up to a point that condensation will not occur as the higher boiling point and/or higher molecular weight compound is admitted to the system.

Therefore, there is a need for a distillation column having a heat pump apparatus that can be used with compounds having a high boiling point.

BRIEF DESCRIPTION OF THE DRAWING

The FIGURE illustrates one embodiment of the process of the present invention.

DETAILED DESCRIPTION

A process and apparatus is provided that allows for startup and operation that will reliably ensure that liquid is not sent to the compressor or formed in the compressor as a gas having a high boiling point is compressed.

This system includes one or more of the following features. It operates using compounds with higher boiling points and/or higher molecular weight, such as xylenes, benzene, toluene, $C_{9+}$ hydrocarbons, or other organic compounds having boiling points at or above 0° C., than previous heat pump applications. Prior art distillation columns using heat pumps typically used lower molecular weight gases with lower boiling points, for example, propane, which has a boiling point of −43.6° F. (−42° C.), propylene, which has a boiling point of −53.7° F. (47.6° C.), normal butane, which has a boiling point of 30.2° F. (−1° C.), and isobutane, which has a boiling point of 10.9° F. (−11.7° C.).

Existing systems utilizing heat pumps with heavier compounds did not provide a method for ensuring reliable operation without the risk of sending liquid to the compressor. They incorporated a single drum for both the receiver and knockout functions. In these cases, condensation would not occur until the heat pump compressor is started and sent through a heat exchanger. In addition, existing designs did not facilitate a start-up procedure that would allow for the compressor to be warmed up prior to admitting higher boiling point compounds to prevent condensation within or upstream of the compressor and avoid compressor damage.

In the present method and apparatus, the compound being compressed would be a liquid at 0° C., so additional consideration of keeping liquid out of the compressor is required. The process and apparatus ensure high on-stream reliability of a complex that requires a heat pump which is using a compound having a high boiling point, such as xylenes. If the compressor is required to be shutdown, it can be isolated from the distillation column and receiver while the column is allowed to continue to operate using an auxiliary reboiler for constant heat input. The isolated heat pump can be started up and heated to the normal process temperature, so that when the heavy vapor is charged to the heat pump, it does not immediately condense into liquid causing damage to the compressor.

Because the compressor operates at much more severe conditions compared to prior heat pump compressors, the likelihood of a shutdown may be greater. This configuration mitigates the risk of a compressor shutdown, planned or unplanned, by allowing the distillation column to continue to operate using the auxiliary reboiler. It also allows for operation of the column to continue even if there are delays in being able to start the compressor. With the configurations in prior art, in the event of a compressor shutdown, it would likely take several days to restart the heat pump compressor and establish normal operation of the column. For applications where the heat pump is on the column providing the main product stream (e.g., para-xylene), the impact of needing several days to restart the plant can have a significant financial impact. With the process and apparatus of the present application, there may be no interruption of production, or only a few hours at most.

The process and apparatus can be used for any system using the vapor of a compound having a high boiling point, including, but not limited to, xylenes, benzene, toluene, $C_{9+}$ hydrocarbons, or other organic compounds having boiling points at or above 0° C. By "compounds having high boiling points" we mean that the boiling point is at or above 0° C. Compounds having a high boiling point would also typically have 5 or more carbons. By "high boiling point vapor" we mean the vapor of a compound having a high boiling point.

The high boiling point vapor is used in the heat pump during normal operation of the column. As part of the startup steps, a transition occurs whereby a gas which is non-condensable and inert to the hydrocarbons in the process (inert non-condensable gas) is used for startup in order to warm-up the compressor. Suitable gases include, but are not limited to, gases typically found in a refinery, including nitrogen, hydrogen, methane, fuel gas, or other typically non-condensable compounds that are inert to the process and hydrocarbons being separated.

When the system is warmed up sufficiently that the high boiling point vapor will not condense in the compressor, the inert non-condensable gas is displaced by the high boiling point vapor. The design provides for the heat pump compressor to be operated and installed on a short loop where it can be bypassed by the column overhead system. In this way, an auxiliary reboiler can begin warm-up of the distillation column and establish normal operation while not being tied to the operation of the heat pump compressor. When the heat pump compressor is available, its system piping will be purged with the inert non-condensable gas and pressurized. The compressor will be started up, and the system piping warmed to the normal operating temperature with the inert non-condensable gas, using a heat exchanger on the suction line to the compressor to provide additional heat.

When the compressor suction temperature and pressure are stable at target conditions, vapors from the already-running column overhead will be introduced into the suction line. The heat pump loop will be vented on pressure control. This will continue until the composition has transitioned from the inert non-condensable gas to the high boiling point vapor. At this point, vapor from the column overhead will be routed to the compressor suction, the compressor discharge gas will be routed to the primary reboiler, and the startup line to a startup condenser will be blocked, forcing gas through the heat pump compressor instead.

In the case of a heat pump compressor shutdown, the compressor short loop will be isolated from the overhead line. The startup condenser will be restarted and the overhead vapors will be sent through the startup condenser on the way to the receiver. The auxiliary reboiler will take over on column bottoms level control, and the primary reboiler will be isolated at its condensate discharge. In this way, the distillation column function can be continued with minimal interruption, until the heat pump compressor can be purged and restarted.

Another advantage of the present process and apparatus is that it reduces the use of external heat sources. Conventionally, separation of heavier boiling components is accomplished using relatively high pressure steam utilizing available process heat from elsewhere in the plant or from a fuel fired heater. Using a heat pump allows for the use of electrical energy to affect the separation.

One aspect of the invention is a process for operating a distillation column including a heat pump using a high boiling point liquid. In one embodiment, the process comprises: providing a distillation column having an inlet, an overhead outlet, and a bottom outlet, the distillation column having a primary reboiler and an auxiliary reboiler; the overhead outlet of the distillation column being in selective upstream communication with a receiver; the overhead outlet of the distillation column being in selective upstream communication with a suction drum; the suction drum being in selective upstream communication with the receiver; the suction drum being in upstream communication with a heat pump; the heat pump being in selective upstream communication with the primary reboiler; and the primary reboiler being in selective upstream communication with the receiver; isolating the suction drum from the overhead product vapor stream and the receiver, and isolating the primary reboiler from the receiver; providing heat to the distillation column using the auxiliary reboiler; separating a high boiling point liquid feed stream comprising in the distillation column into an overhead product vapor stream and a liquid bottom stream; sending the overhead vapor product stream from the distillation column directly to the receiver; introducing the inert non-condensable gas into a loop comprising the isolated suction drum and the heat pump to raise a temperature of the loop to a predetermined temperature; when the loop reaches the predetermined temperature, introducing the overhead product vapor stream into the loop and replacing the the inert non-condensable gas with the overhead product vapor stream forming a circulating vapor stream, and wherein the overhead product vapor stream remains in the vapor phase in the heat pump; sending a heat pump discharge to the primary reboiler to provide heat to the distillation column; sending a primary reboiler condensate discharge to the receiver; reducing an amount of the overhead product vapor stream sent directly to the receiver; reducing the heat provided by the auxiliary reboiler; and recovering product from the receiver.

The term "upstream communication" means that at least a portion of the material flowing from the subject in upstream communication may operatively flow to the object with which it communicates. The term "selective" means that flow is permitted at certain times and blocked at other times.

The term "directly," means that the overhead vapor product stream is sent to the receiver without going through the suction drum or the heat pump. It can be sent through a condenser, for example, and then to the receiver.

In some embodiments, the process further comprises: heating one or more of the inert non-condensable gas or the overhead product vapor stream between the suction drum and the heat pump.

In some embodiments, the process further comprises: bypassing a portion of the heat pump discharge around the suction drum.

In some embodiments, the process further comprises: condensing the overhead product vapor stream to form a condensed product stream; and wherein sending the overhead vapor product stream from the distillation column directly to the receiver comprises sending the condensed product stream to the receiver.

In some embodiments, when the primary reboiler provides heat to the distillation column, the auxiliary reboiler provides less than 10% of the heat to the distillation column.

In some embodiments, the process further comprises: condensing at least a portion of the circulating vapor stream between the heat pump discharge and the suction drum.

In some embodiments, the process further comprises: introducing the inert non-condensable gas into a portion of a line between the heat pump discharge and the primary reboiler to warm the line.

In some embodiments, the process further comprising at least one of: sensing at least one parameter of the process and generating a signal or data from the sensing; generating and transmitting a signal; or generating and transmitting data.

In some embodiments, the process further comprises: venting the inert non-condensable gas from the loop when the inert non-condensable gas is replaced with the overhead product vapor stream.

Another aspect of the invention is a process for operating a distillation column including a heat pump using a high boiling point liquid. In one embodiment, the process comprises: providing a distillation column having an inlet, an overhead outlet, and a bottom outlet, the distillation column having a primary reboiler and an auxiliary reboiler; the overhead outlet of the distillation column being in selective upstream communication with a receiver; the overhead outlet of the distillation column being in selective upstream communication with a suction drum; the suction drum being in selective upstream communication with the receiver; the suction drum being in upstream communication with a heat pump; the heat pump being in selective upstream communication with the primary reboiler; and the primary reboiler being in selective upstream communication with the receiver; selectively providing heat to the distillation column using the primary reboiler or the auxiliary reboiler to separate a high boiling point liquid into an overhead product vapor stream and a liquid bottom stream; when the heat to the distillation column is provided using the primary reboiler: selectively sending the overhead product vapor stream from the distillation column to the suction drum; sending a vapor stream from the suction drum to the heat pump, wherein the vapor stream remains in the vapor phase in the heat pump; sending a heat pump discharge to the primary reboiler to provide heat to the distillation column; sending a primary reboiler condensate discharge to the receiver; recovering product from the receiver; when the heat to the distillation column is provided using the auxiliary reboiler: isolating the suction drum from the overhead product vapor stream and the receiver, and isolating the primary reboiler from the receiver; selectively sending the overhead vapor product stream from the distillation column directly to the receiver; recovering product from the receiver.

In some embodiments, the process further comprises: when the heat to the distillation column is provided using the auxiliary reboiler: introducing the inert non-condensable gas into a loop comprising the isolated suction drum and the heat pump to raise a temperature of the loop to a predetermined temperature; when the loop reaches the predetermined temperature, introducing the overhead product vapor stream into the loop and replacing the inert non-condensable gas with the overhead product vapor stream wherein the overhead product vapor stream remains in the vapor phase in the heat pump.

In some embodiments, the process further comprises: introducing the inert non-condensable gas into a portion of a line between the heat pump discharge and the primary reboiler to warm the line.

In some embodiments, the process further comprises: heating one or more of the inert non-condensable gas or the vapor stream between the suction drum and the heat pump.

In some embodiments, the process further comprises: bypassing a portion of the heat pump discharge around the suction drum.

In some embodiments, the process further comprises: wherein when the heat to the distillation column is provided using the auxiliary reboiler: condensing the overhead product vapor stream to form a condensed product stream; and wherein selectively sending the overhead vapor product stream from the distillation column directly to the receiver comprises sending the condensed product stream to the receiver.

In some embodiments, when the primary reboiler provides heat to the distillation column, the auxiliary reboiler provides less than 10% of the heat to the distillation column.

In some embodiments, the process further comprises: condensing at least a portion of the circulating vapor stream between the heat pump discharge and the suction drum.

In some embodiments, the process further comprises: venting the inert non-condensable gas from the loop when the inert non-condensable gas is replaced with the overhead product vapor stream.

Another aspect of the invention is an apparatus. In one embodiment, the apparatus comprises: a distillation column having an inlet, an overhead outlet, and a bottom outlet; a primary reboiler in selective thermal communication with the distillation column; an auxiliary reboiler in selective thermal communication with the distillation column; the overhead outlet of the distillation column being in selective upstream communication with a receiver; the overhead outlet of the distillation column being in selective upstream communication with a suction drum; the suction drum being in selective upstream communication with the receiver; the suction drum being in upstream communication with a heat pump; the heat pump being in selective upstream communication with the primary reboiler; and the primary reboiler being in selective upstream communication with the receiver.

In some embodiments, the apparatus further comprises one or more of: a heat exchanger positioned between the suction drum and a suction side of the heat pump; or a condenser positioned between the overhead outlet and the receiver.

The FIGURE illustrates one embodiment of the process 100. The process 100 can be part of a larger aromatics complex, such as a Honeywell UOP Parex™ process (not shown). A high boiling point liquid feed stream 105 is sent to distillation column 110. By "high boiling point liquid" we mean a compound having a high boiling point in liquid form. The high boiling point liquid feed stream 105 can contain para-xylene, for example. The source of the high boiling point liquid feed stream 105 can be a xylene separation process. The source of high boiling liquid feed streams containing benzene, toluene, or $C_{9+}$ hydrocarbons could be upstream distillation columns. Other organic compounds having boiling points at or above 0° C. could come from plants or units within plants performing hydrocarbon conversion or separation processes.

The high boiling point liquid feed stream 105 is separated in distillation column 110 into an overhead product vapor stream 115 and a bottom stream 120. There are a primary reboiler 125 and an auxiliary reboiler 130 at the bottom of the distillation column 110.

The inlet stream to the reboilers can be a portion of the bottom stream 120 from the distillation column 110 or it can come directly from the distillation column 110.

As shown, the primary reboiler 125 and the auxiliary reboiler 130 are at the bottom of the distillation column 110. Alternatively, the primary reboiler 125 and the auxiliary reboiler 130 could be used for reflux at the top of the column, or as the side reboiler service at an elevation between the top and bottom of the distillation column 110.

During start-up of the distillation column 110 or when the heat pump is not operational, the source of heat to the distillation column 110 is the auxiliary reboiler 130. A portion 135 of the bottom stream 120 is sent to the auxiliary reboiler 130, and the heated stream 140 is returned to the distillation column 110.

The overhead product vapor stream 115 is sent directly to the receiver 145. There can optionally be a condenser 150 on the line between the overhead outlet of the distillation column 110 and the receiver 145. The condensed vapor from the condenser 150 is sent to the receiver 145. The product stream 155 from the receiver 145 is recovered.

A portion 160 of the product stream 155 may be sent back to the distillation column 110 for reflux.

During this time, the heat pump loop, which includes suction drum 165 and heat pump 170, is isolated from the overhead product vapor stream 115. Valve 175 on line 180 to the suction drum 165 is closed. Valve 185 on line 190 from the suction drum 165 to the receiver 145 is closed. Valve 195 on line 200 from the primary reboiler 125 to the receiver 145 is also closed.

When the heat pump is ready to be started, the heat pump loop is charged with the inert non-condensable gas, such as nitrogen, and the heat pump 170 is started which warms the lines. The nitrogen flows in the heat pump loop from the discharge side of the heat pump 170 through line 205, 210, 215 bypassing suction drum 165 to heat exchanger 220 where the temperature is increased further. The nitrogen then flows through line 222 to the suction side of the heat pump 170.

The bypass may not be complete; a portion of the nitrogen may flow through line 225 and condenser 230 to the suction drum 165. The function of condenser 230 during start-up is as a cooler. Another portion of the nitrogen can flow through line 235 to the primary reboiler 125 to warm line 235.

When the heat pump loop reaches the desired temperature so that the product vapor will not condense in the heat pump 170, valve 175 on line 180 is opened, allowing some of the overhead product vapor stream to flow into suction drum 165 and into the heat pump loop through line 240. The nitrogen is vented from the heat pump loop as the overhead as the overhead product vapor stream is introduced. The amount of overhead product vapor stream is increased until the nitrogen has been replaced in the heat pump loop.

At that point, valve 245 can be partially or completely closed, reducing or stopping the flow of the overhead product vapor stream 115 to the receiver 145. Valves 185 and 195 are also opened.

The overhead product vapor stream 115 flows through line 180 to the suction drum 165, through lines 240, 215 to heat exchanger 220. It then flows through line 222 to the suction side of the heat pump 170.

Other methods of heating the overhead product vapor stream 115 may include using the shaft work from the heat pump compressor itself alone, without a separate heater or heat exchanger. In such cases, an expansion valve may be included on the suction line to the heat pump compressor to provide superheat to the condensable vapor circulating during normal operation.

From the discharge side of the heat pump 170, the vapor flows through line 205 and 235 to the primary reboiler 125. Liquid from the distillation column 110 is sent in line 237 to the primary reboiler 125 where it is heated and returned to the distillation column in line 239.

The primary reboiler condensate discharge flows through line 200 to heat exchanger 250 and to the receiver 145. A portion of the vapor may flow through line 225 and condenser 230 to the suction drum 165. The function of condenser 230 during normal operation is as a condenser.

Control valves on lines 210 and 225 can be used to control the pressure in the heat pump loop.

When the primary reboiler 125 is operational, the heat from the auxiliary reboiler 130 is reduced. The amount of heat from the auxiliary reboiler 130 may be reduced to less than 25% of the total amount of heat from the primary reboiler 125 and the auxiliary reboiler 130, or less than 20%, or less than 15%, or less than 10%, or less than 5%.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems 255. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

Specific Embodiments

While the following is described in conjunction with specific embodiments, it will be understood that this description is intended to illustrate and not limit the scope of the preceding description and the appended claims.

A first embodiment of the invention is a process for operating a distillation column including a heat pump using a high boiling point liquid comprising providing a distillation column having an inlet, an overhead outlet, and a bottom outlet, the distillation column having a primary reboiler and an auxiliary reboiler; the overhead outlet of the distillation column being in selective upstream communication with a receiver; the overhead outlet of the distillation column being in selective upstream communication with a suction drum; the suction drum being in selective upstream communication with the receiver; the suction drum being in upstream communication with a heat pump; the heat pump being in upstream communication with the primary reboiler; and the primary reboiler being in selective upstream communication with the receiver; isolating the suction drum from the overhead product vapor stream and the receiver, and isolating the primary reboiler from the receiver; providing heat to the distillation column using the auxiliary reboiler; separating a high boiling point liquid feed stream comprising in the distillation column into an overhead product vapor stream and a liquid bottom stream; sending the overhead vapor product stream from the distillation column directly to the receiver; introducing nitrogen into a loop comprising the isolated suction drum and the heat pump to raise a temperature of the loop to a predetermined temperature; when the loop reaches the predetermined temperature, introducing the overhead product vapor stream into the loop and replacing the nitrogen with the overhead product vapor stream forming a circulating vapor stream, and wherein the overhead product vapor stream remains in the vapor phase in the heat pump; sending a heat pump discharge to the primary reboiler to provide heat to the distillation column; sending a primary reboiler condensate discharge to the receiver; reducing an amount of the overhead product vapor stream sent directly to the receiver; reducing the heat provided by the auxiliary reboiler; and recovering product from the receiver. An embodiment of the invention is one, any or all of prior embodiments in this paragraph up through the first embodiment in this paragraph further comprising heating one or more of the nitrogen or the overhead product vapor stream between the suction drum and the heat pump. An embodiment of the invention is one, any or all of prior embodiments in this paragraph up through the first embodiment in this paragraph further comprising bypassing a portion of the heat pump discharge around the suction drum. An embodiment of the invention is one, any or all of prior embodiments in this paragraph up through the first embodiment in this paragraph further comprising condensing the overhead product vapor stream to form a condensed product stream; and wherein sending the overhead vapor product stream from the distillation column directly to the receiver comprises sending the condensed product stream to the receiver. An embodiment of the invention is one, any or all of prior embodiments in this paragraph up through the first embodiment in this paragraph wherein when the primary reboiler provides heat to the distillation column, the auxiliary reboiler provides less than 10% of the heat to the distillation column. An embodiment of the invention is one, any or all of prior embodiments in this paragraph up through the first embodiment in this paragraph further comprising condensing at least a portion of the circulating vapor stream between the heat pump discharge and the suction drum. An embodiment of the invention is one, any or all of prior embodiments in this paragraph up through the first embodiment in this paragraph further comprising introducing nitrogen into a portion of a line between the heat pump discharge and the primary reboiler to warm the line. An embodiment of the invention is one, any or all of prior embodiments in this paragraph up through the first embodiment in this paragraph, further comprising at least one of sensing at least one parameter of the process and generating a signal or data from the sensing; generating and transmitting a signal; or generating and transmitting data. An embodiment of the invention is one, any or all of prior embodiments in this paragraph up through the first embodiment in this paragraph further comprising venting the nitrogen from the loop when the nitrogen is replaced with the overhead product vapor stream.

A second embodiment of the invention is a process for operating a distillation column including a heat pump using a high boiling point liquid comprising providing a distillation column having an inlet, an overhead outlet, and a bottom outlet, the distillation column having a primary reboiler and an auxiliary reboiler; the overhead outlet of the distillation column being in selective upstream communication with a receiver; the overhead outlet of the distillation column being in selective upstream communication with a suction drum; the suction drum being in selective upstream communication with the receiver; the suction drum being in upstream communication with a heat pump; the heat pump being in upstream communication with the primary reboiler; and the primary reboiler being in selective upstream communication with the receiver; selectively providing heat to the distillation column using the primary reboiler or the auxiliary reboiler to separate a high boiling point liquid into an overhead product vapor stream and a liquid bottom stream; when the heat to the distillation column is provided using the primary reboiler selectively sending the overhead product vapor stream from the distillation column to the suction drum; sending a vapor stream from the suction drum to the heat pump, wherein the vapor stream remains in the vapor phase in the heat pump; sending a heat pump discharge to the primary reboiler to provide heat to the distillation column; sending a primary reboiler condensate discharge to the receiver; recovering product from the receiver; when the heat to the distillation column is provided using the auxiliary reboiler isolating the suction drum from the overhead product vapor stream and the receiver, and isolating the primary reboiler from the receiver; selectively sending the overhead vapor product stream from the distillation column directly to the receiver; recovering product from the receiver. An embodiment of the invention is one, any or all of prior embodiments in this paragraph up through the second embodiment in this paragraph further comprising when the heat to the distillation column is provided using the auxiliary reboiler introducing nitrogen into a loop comprising the isolated suction drum and the heat pump to raise a temperature of the loop to a predetermined temperature; when the loop reaches the predetermined temperature, introducing the overhead product vapor stream into the loop and replacing the nitrogen with the overhead product vapor stream wherein the overhead product vapor stream remains in the vapor phase in the heat pump. An embodiment of the invention is one, any or all of prior embodiments in this paragraph up through the second embodiment in this paragraph further comprising introducing nitrogen into a portion of a line between the heat pump discharge and the primary reboiler to warm the line. An embodiment of the invention is one, any or all of prior embodiments in this paragraph up through the second embodiment in this paragraph further comprising heating one or more of the nitrogen or the vapor stream between the suction drum and the heat pump. An embodiment of the invention is one, any or all of prior embodiments in this paragraph up through the second embodiment in this paragraph further comprising bypassing a portion of the heat pump discharge around the suction drum. An embodiment of the invention is one, any or all of prior embodiments in this paragraph up through the second embodiment in this paragraph further comprising wherein when the heat to the distillation column is provided using the auxiliary reboiler condensing the overhead product vapor stream to form a condensed product stream; and wherein selectively sending the overhead vapor product stream from the distillation column directly to the receiver comprises sending the condensed product stream to the receiver. An embodiment of the invention is one, any or all of prior embodiments in this paragraph up through the second embodiment in this paragraph wherein when the primary reboiler provides heat to the distillation column, the auxiliary reboiler provides less than 10% of the heat to the distillation column. An embodiment of the invention is one, any or all of prior embodiments in this paragraph up through the second embodiment in this paragraph further comprising condensing at least a portion of the circulating vapor stream between the heat pump discharge and the suction drum. An embodiment of the invention is one, any or all of prior embodiments in this paragraph up through the second embodiment in this paragraph further comprising venting the nitrogen from the loop when the nitrogen is replaced with the overhead product vapor stream.

A third embodiment of the invention is an apparatus comprising a distillation column having an inlet, an overhead outlet, and a bottom outlet; a primary reboiler in selective thermal communication with the distillation column; an auxiliary reboiler in selective thermal communication with the distillation column; the overhead outlet of the distillation column being in selective upstream communication with a receiver; the overhead outlet of the distillation column being in selective upstream communication with a suction drum; the suction drum being in selective upstream communication with the receiver; the suction drum being in upstream communication with a heat pump; the heat pump being in upstream communication with the primary reboiler; and the primary reboiler being in selective upstream communication with the receiver. An embodiment of the invention is one, any or all of prior embodiments in this paragraph up through the third embodiment in this paragraph further comprising one or more of a heat exchanger positioned between the suction drum and a suction side of the heat pump; or a condenser positioned between the overhead outlet and the receiver.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for operating a distillation column including a heat pump using a high boiling point liquid comprising:
   providing a distillation column having an inlet, an overhead outlet, and a bottom outlet, the distillation column having a primary reboiler and an auxiliary reboiler; the overhead outlet of the distillation column being in selective upstream communication with a receiver; the overhead outlet of the distillation column being in selective upstream communication with a suction drum; the suction drum being in selective upstream communication with the receiver; the suction drum being in upstream communication with a heat pump; the heat pump being in selective upstream communication with the primary reboiler; and the primary reboiler being in selective upstream communication with the receiver;
   providing heat to the distillation column using the auxiliary reboiler;
   separating a high boiling point liquid feed stream in the distillation column into an overhead product vapor stream and a liquid bottom stream;
   isolating the suction drum from the overhead product vapor stream and the receiver, and isolating the primary reboiler from the receiver;
   sending the overhead vapor product stream from the distillation column directly to the receiver;
   introducing an inert non-condensable gas into a loop comprising the isolated suction drum and the heat pump to raise a temperature of the loop to a predetermined temperature;
   when the temperature of the loop reaches the predetermined temperature, introducing a portion of the overhead product vapor stream into the loop while reducing an amount of the overhead product vapor stream sent directly to the receiver and replacing the inert non-condensable gas with the overhead product vapor stream forming a circulating vapor stream, wherein the circulating vapor stream remains in the vapor phase in the heat pump;
   sending a heat pump discharge to the primary reboiler to provide additional heat to the distillation column;
   sending a primary reboiler condensate discharge to the receiver;
   reducing the amount of heat to the distillation column provided by the auxiliary reboiler; and
   recovering a product from the receiver.

2. The process of claim 1 further comprising:
   heating one or more of the inert non-condensable gas or the circulating vapor stream between the suction drum and the heat pump.

3. The process of claim 1 further comprising:
   bypassing a portion of the heat pump discharge around the suction drum.

4. The process of claim 1 further comprising:
   condensing the overhead product vapor stream to form a condensed product stream; and
   wherein sending the overhead vapor product stream from the distillation column directly to the receiver comprises sending the condensed product stream to the receiver.

5. The process of claim 1 wherein after reducing the amount of heat to the distillation column provided by the auxiliary reboiler, when the primary reboiler provides heat to the distillation column, the auxiliary reboiler provides less than 10% of the heat to the distillation column.

6. The process of claim 1 further comprising:
   condensing at least a portion of the circulating vapor stream between the heat pump discharge and the suction drum.

7. The process of claim 1 further comprising:
   introducing the inert non-condensable gas into a portion of a line between the heat pump discharge and the primary reboiler to warm the line.

8. The process of claim 1, further comprising at least one of:
   sensing at least one parameter of the process and generating a signal or data from the sensing;
   generating and transmitting a signal; or
   generating and transmitting data.

9. The process of claim 1 further comprising:
   venting the inert non-condensable gas from the loop when the inert non-condensable gas is replaced with the overhead product vapor stream.

10. A process for operating a distillation column including a heat pump using a high boiling point liquid comprising:
    providing a distillation column having an inlet, an overhead outlet, and a bottom outlet, the distillation column having a primary reboiler and an auxiliary reboiler; the overhead outlet of the distillation column being in selective upstream communication with a receiver; the overhead outlet of the distillation column being in selective upstream communication with a suction drum; the suction drum being in selective upstream communication with the receiver; the suction drum being in to upstream communication with a heat pump; the heat pump being in selective upstream communication with the primary reboiler; and the primary reboiler being in selective upstream communication with the receiver;
    selectively providing heat to the distillation column using the primary reboiler or the auxiliary reboiler to separate a high boiling point liquid into an overhead product vapor stream and a liquid bottom stream by:
       providing heat to the distillation column using the auxiliary reboiler;
       selectively sending at least a portion of an overhead vapor product stream from the distillation column directly to the receiver;
       recovering a first portion of a product from the receiver;
       isolating the suction drum from the overhead product vapor stream and the receiver, and isolating the primary reboiler from the receiver;

switching from providing heat to the distillation column using the auxiliary reboiler to providing heat to the distillation column using the primary reboiler by:
introducing an inert non-condensable gas into a loop comprising the heat pump to raise a to a predetermined temperature;
when the temperature of the loop reaches the predetermined temperature, introducing a portion of the overhead product vapor stream into the loop while reducing an amount of the overhead product vapor stream sent directly to receiver and replacing the inert non-condensable gas with the overhead product vapor stream to form a recirculating vapor stream in a heat loop comprising the heat pump;
selectively sending at least a portion of the overhead product vapor stream from the distillation column to the suction drum;
sending a vapor stream from the suction drum to the heat pump and the recirculating vapor stream, wherein the recirculating vapor stream remains in the vapor phase in the heat pump;
sending a heat pump discharge to the primary reboiler to provide heat to the distillation column;
sending a primary reboiler condensate discharge to the receiver; and
recovering a second portion of a product from the receiver.

11. The process of claim 10 further comprising:
introducing the inert non-condensable gas into a portion of a line between the heat pump discharge and the primary reboiler to warm the line.

12. The process of claim 10 further comprising:
heating one or more of the inert non-condensable gas or the circulating vapor stream between the suction drum and the heat pump.

13. The process of claim 10 further comprising:
bypassing a portion of the heat pump discharge around the suction drum.

14. The process of claim 10 further comprising:
wherein when the heat to the distillation column is provided using the auxiliary reboiler:
condensing the overhead product vapor stream to form a condensed product stream; and
wherein selectively sending the overhead vapor product stream from the distillation column directly to the receiver comprises sending the condensed product stream to the receiver.

15. The process of claim 10 wherein when the primary reboiler provides the to the distillation column, the auxiliary reboiler provides less than 10% of the heat to the distillation column.

16. The process of claim 10 further comprising condensing at least a portion of the circulating vapor stream between the heat pump discharge and the suction drum.

17. The process of claim 10 further comprising:
venting the inert non-condensable gas from the loop when the inert non-condensable gas is replaced with the overhead product vapor stream.

\* \* \* \* \*